(12) United States Patent
Farrell et al.

(10) Patent No.: US 8,216,168 B2
(45) Date of Patent: Jul. 10, 2012

(54) ORTHOTIC DEVICE SPANNING ELBOW

(75) Inventors: John F. Farrell, Charlotte, NC (US); Henry B. Hoffman, Charlotte, NC (US); Ian D. Kovacevich, Charlotte, NC (US)

(73) Assignee: Saebo, Inc., Charlotte, NC (US)

( * ) Notice: Subject to any disclaimer, the term of this patent is extended or adjusted under 35 U.S.C. 154(b) by 776 days.

(21) Appl. No.: 12/329,169

(22) Filed: Dec. 5, 2008

(65) Prior Publication Data

US 2009/0149790 A1    Jun. 11, 2009

Related U.S. Application Data

(60) Provisional application No. 60/992,370, filed on Dec. 5, 2007.

(51) Int. Cl.
*A61F 5/00* (2006.01)
*A61F 13/00* (2006.01)

(52) U.S. Cl. .............. 602/20; 602/5; 602/21; 602/60; 602/61; 602/62

(58) Field of Classification Search .............. 602/5, 16, 602/26, 20–22, 60–63
See application file for complete search history.

(56) References Cited

U.S. PATENT DOCUMENTS

| | | | | |
|---|---|---|---|---|
| 4,875,677 A | * | 10/1989 | Tetreault | 473/458 |
| 2003/0125651 A1 | * | 7/2003 | Hopkins et al. | 602/20 |
| 2005/0165337 A1 | * | 7/2005 | Weiss | 602/20 |

* cited by examiner

*Primary Examiner* — Kim M Lewis
(74) *Attorney, Agent, or Firm* — Nelson Mullins Riley & Scarborough, LLP

(57) ABSTRACT

An orthotic for mounting on a user's arm comprises an upper cuff that is removeably attachable to the user's arm at a point above the elbow joint. A lower cuff is removeably attachable to the user's arm at a point below the elbow joint, and is rotationally fixed to the forearm. At least one flexible elongated member having a first end that is releasably coupled to the upper cuff and an opposite second end that is releasably coupled to the lower cuff. The upper cuff and the lower cuff are configured to move in more than one plane with respect to one another.

15 Claims, 16 Drawing Sheets

ORTHOTIC DEVICE SPANNING ELBOW

CLAIM OF PRIORITY

This application claims priority to U.S. provisional application Ser. No. 60/992,370, filed Dec. 5, 2007, the entire disclosure of which is incorporated by reference herein.

BACKGROUND OF THE INVENTION

The present invention generally relates to orthotic devices and, in particular, an orthotic device that is designed to span the elbow and that are secured to an arm both above and below the elbow.

Following a neurological injury, a patient often experiences upper limb involvement (hemiparesis). Often times the elbow presents with hypertonia or hypotonia. Hypertonia is when the elbow tends to, stay in the flexed position, and hypotonia is when the elbow is week and hangs down at the side. Hypotonia is often also referred to as flaccid.

Orthotic devices that address the hemiparetic elbow conventionally include an upper component that attaches to the arm above the elbow and a lower component that attaches to the arm below the elbow. Furthermore, the upper component and the lower component are hinged together in pivotable disposition in the area of the elbow, and a biasing member typically biases the upper and lower components toward a particular orientation relative to one another and thereby urges the arm into flexion or extension, as the case may be. An example of such an orthotic device 100 is shown in FIGS. 1-3. In particular, FIG. 1 is an overall perspective view of a conventional elbow orthotic 100; FIG. 2 is a partial perspective view of the orthotic 100 in a flexed position; and FIG. 3 is a partial perspective view of the orthotic 100 in a flexed position. As will be appreciated from review of FIGS. 1-3, upper and lower arm components 102,104 of the orthotic 100 have overlapping portions that are hinged together at an axis 106.

A drawback to such conventional orthotic devices is that they tend to inhibit or otherwise interfere with movement of the forearm between pronation and supination. In this respect, it is important to note that the elbow flexes and extends; however, below the elbow the forearm pronates and supinates, which is to say that the forearm turns the hand palm down and palm up, respectively. This is anatomically done by the physical make up of two bones of the forearm, i.e., the Radius and the Ulna. Another drawback with conventional elbow orthotic devices is that they do not incorporate the hand functionally for grasp and release activities.

An orthotic device in accordance with one or more preferred embodiments of the present invention addresses such drawback.

SUMMARY OF THE INVENTION

The present invention includes many aspects and features.

In an aspect of the invention, an orthotic includes: (a) an upper component configured to be attached to an arm above the elbow; (b) a lower component configured to be attached to an arm below the elbow; and (c) one or more elongate intermediate components connecting the upper component and the lower component together, wherein the one or more intermediate component are elastic and wherein only the one or more intermediate components connect the upper and lower components together.

In another aspect of the invention, an orthotic includes: (a) an upper component configured to be attached to an arm above the elbow; (b) a lower component configured to be attached to an arm below the elbow; and (c) one or more elongate intermediate components connecting the upper component and the lower component together, wherein the one or more intermediate component are elastic and wherein the upper and lower components are not hinged together.

In a feature of one or more of these aspects, the orthotic is an elbow orthotic and is configured to urge the arm into flexion.

In a feature of one or more of these aspects, the orthotic is an elbow orthotic and is configured to urge the arm into extension.

In a feature of one or more of these aspects, the one or more intermediate components is an elastic cord.

In a feature of one or more of these aspects, the one or more intermediate components is a flexible rod.

In a feature of one or more of these aspects, the orthotic further includes a component that is attached to and extends from the upper component and that defines a point of tensional redirection in one of the intermediate components.

Another aspect of the invention is a method of treating a hemiparetic elbow using an orthotic of any of the preceding aspects and features.

Another aspect of the invention is a method of making/assembling the orthotic of any of the preceding aspects and features.

In still yet another aspect, an upper arm component configured to be secured to an upper arm above the elbow and a component attached thereto and extending therefrom and configured to guide a line of tension from the upper arm component to a point of tensional redirection located below the elbow.

In addition to the aforementioned aspects and features of the present invention, the present invention further encompasses the various possible combinations of such aspects and features.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
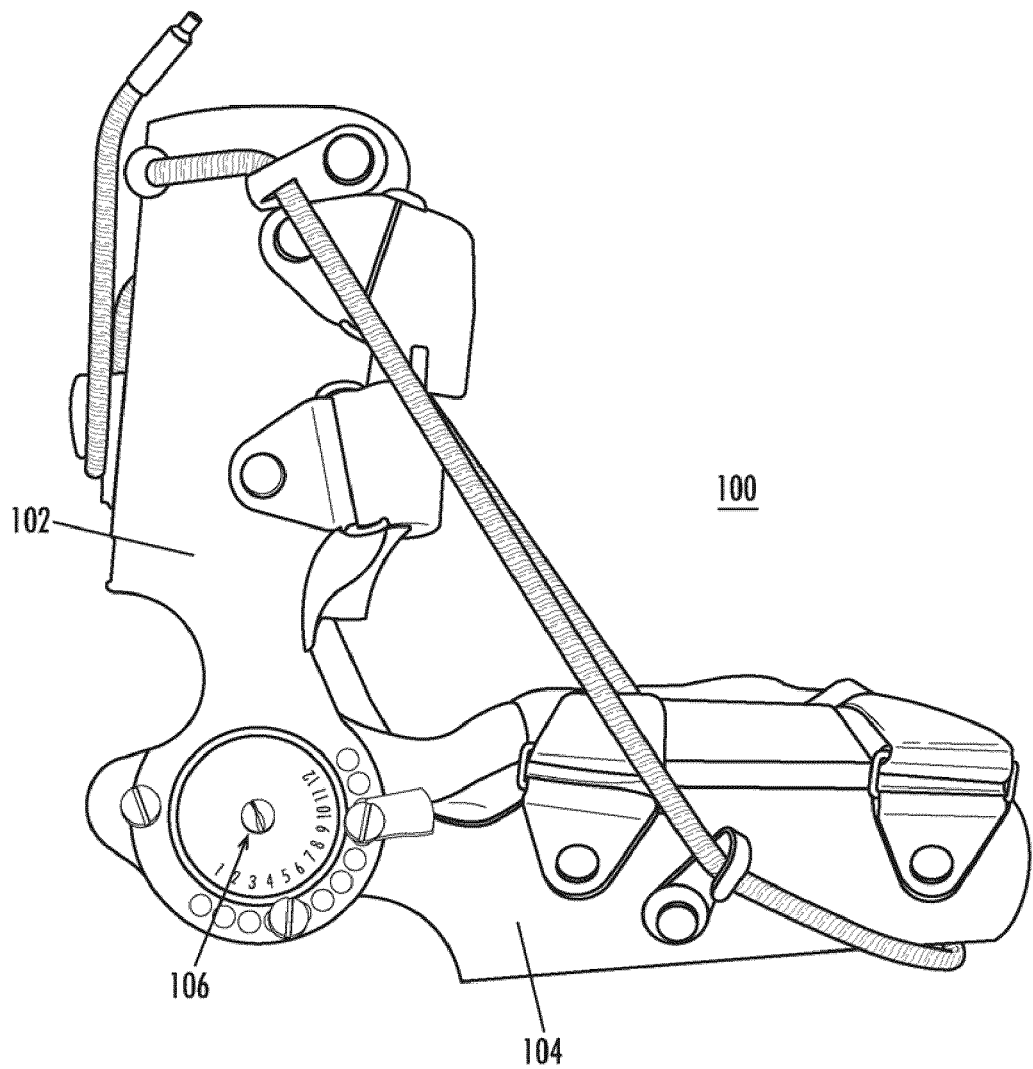
FIG. 1 is an overall perspective view of the conventional elbow orthotic.
Figure 2:
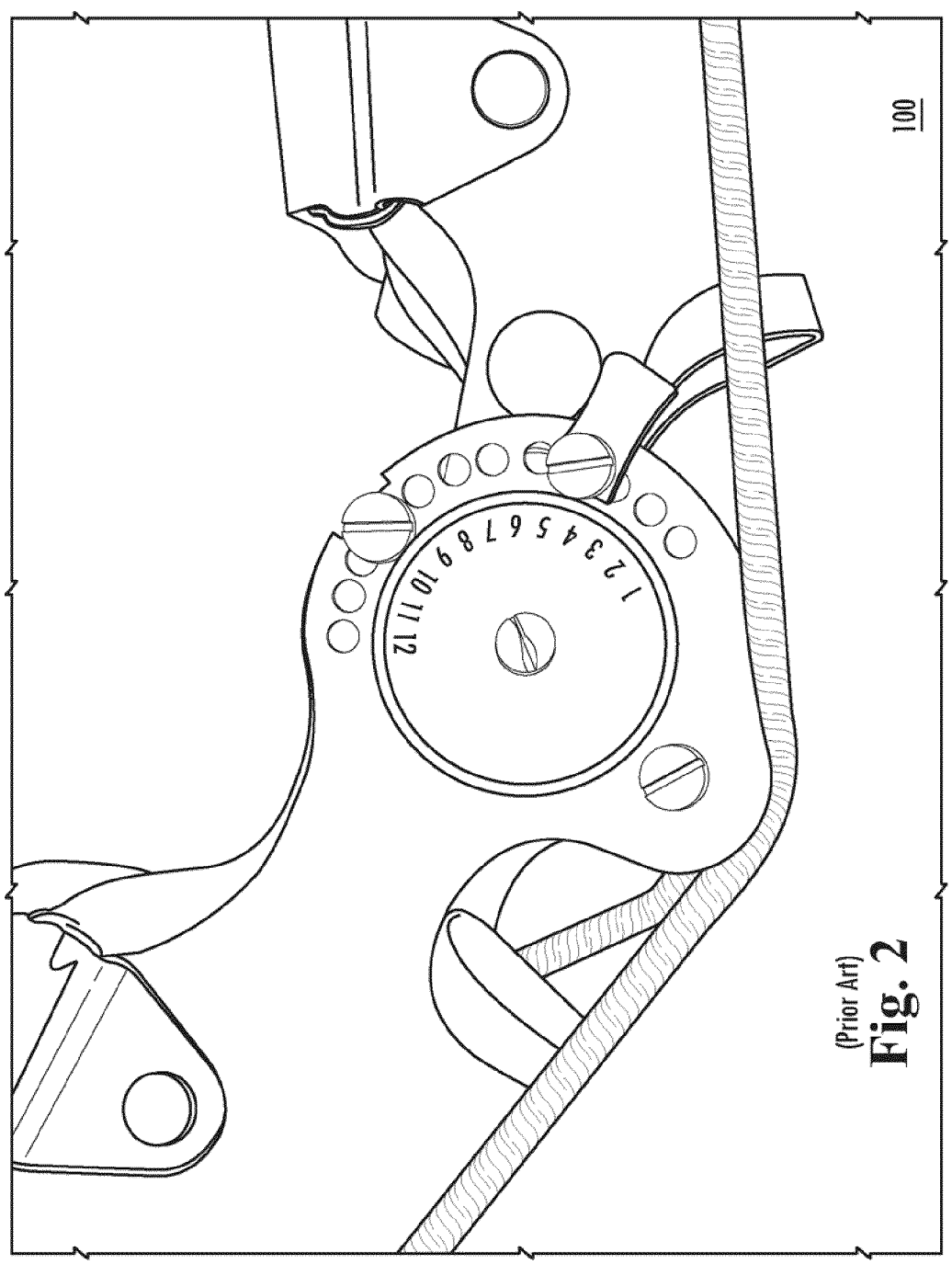
FIG. 2 is a partial perspective view of the orthotic of FIG. 1 in an extended position.
Figure 3:
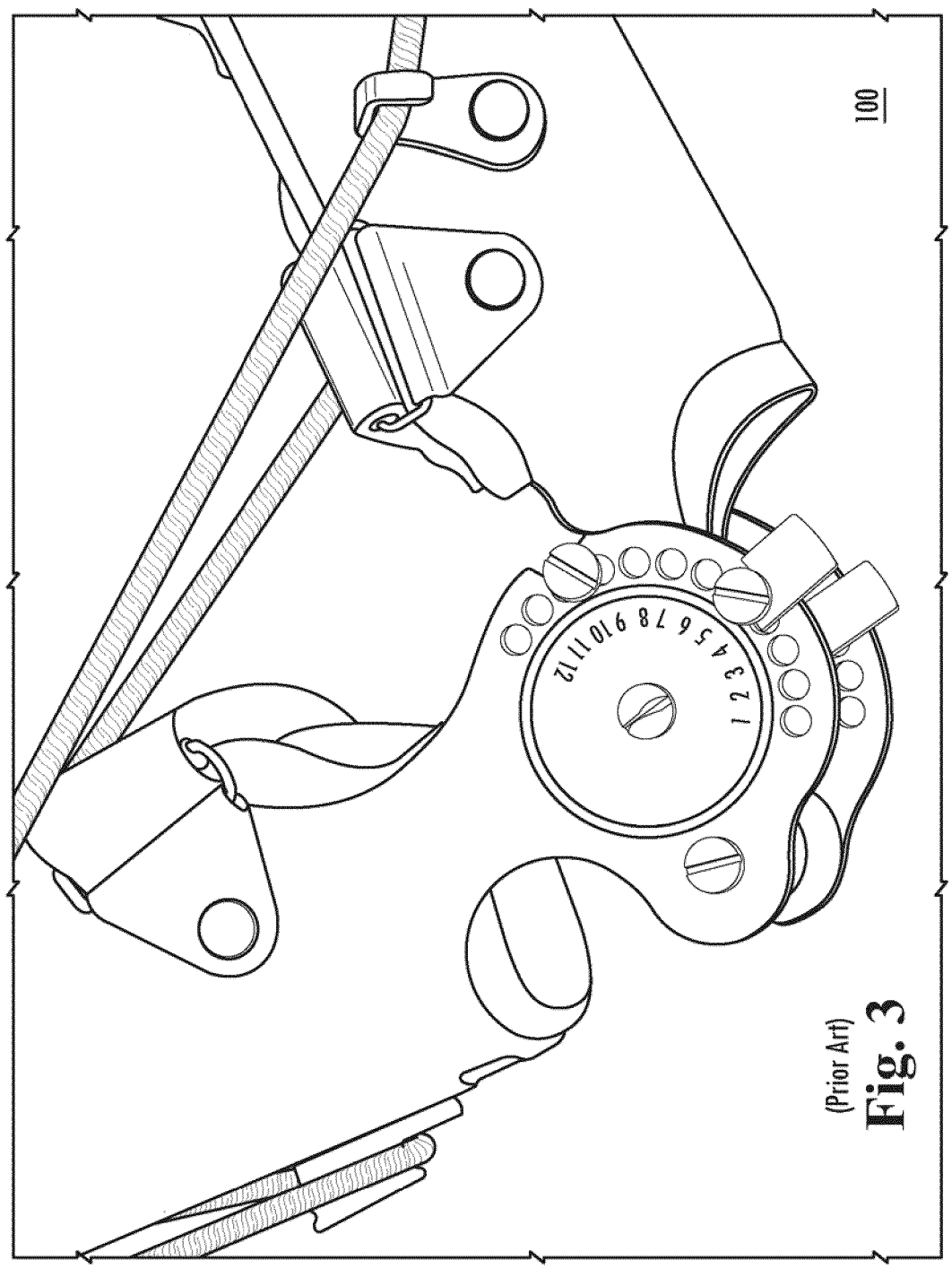
FIG. 3 is a partial perspective view of the orthotic of FIG. 1 in a flexed position

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Figure 4:
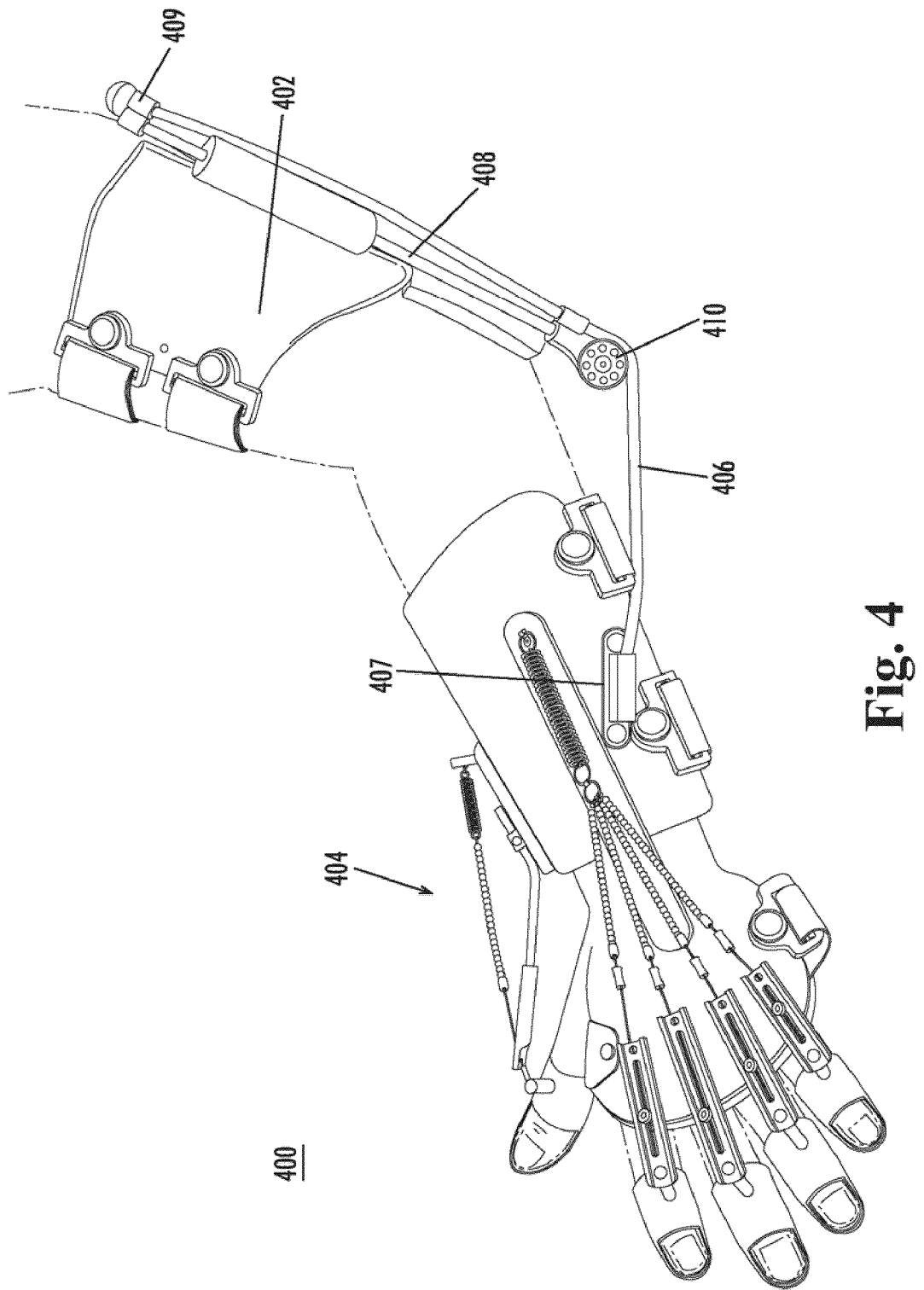
FIG. 4 is a perspective view of an elbow orthotic in accordance with a preferred embodiment of the present invention, wherein the arm is in a partially extended position.
Figure 5:
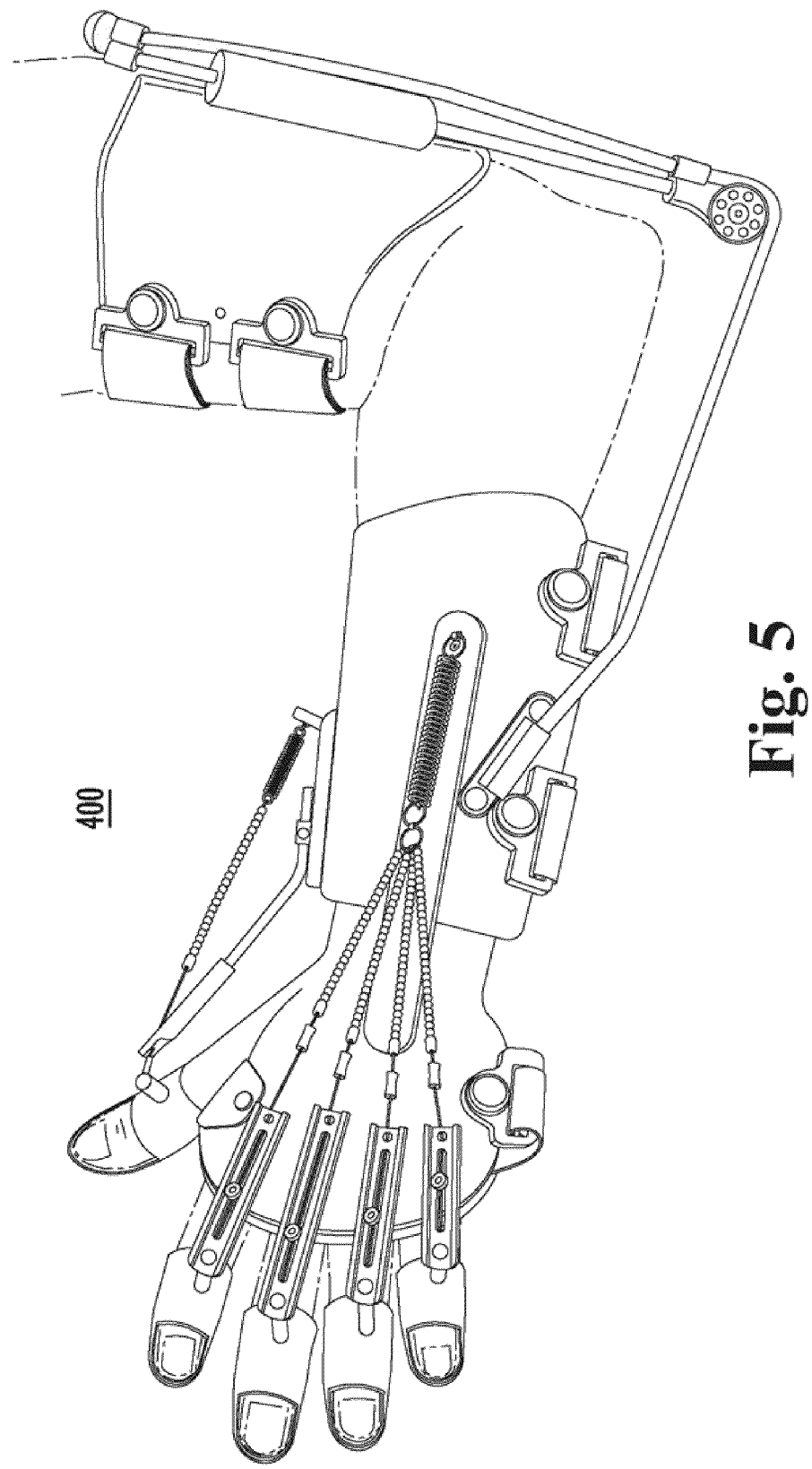
FIG. 5 is a perspective view of the elbow orthotic of FIG. 4, wherein the arm is in a flexed position.
Figure 6:
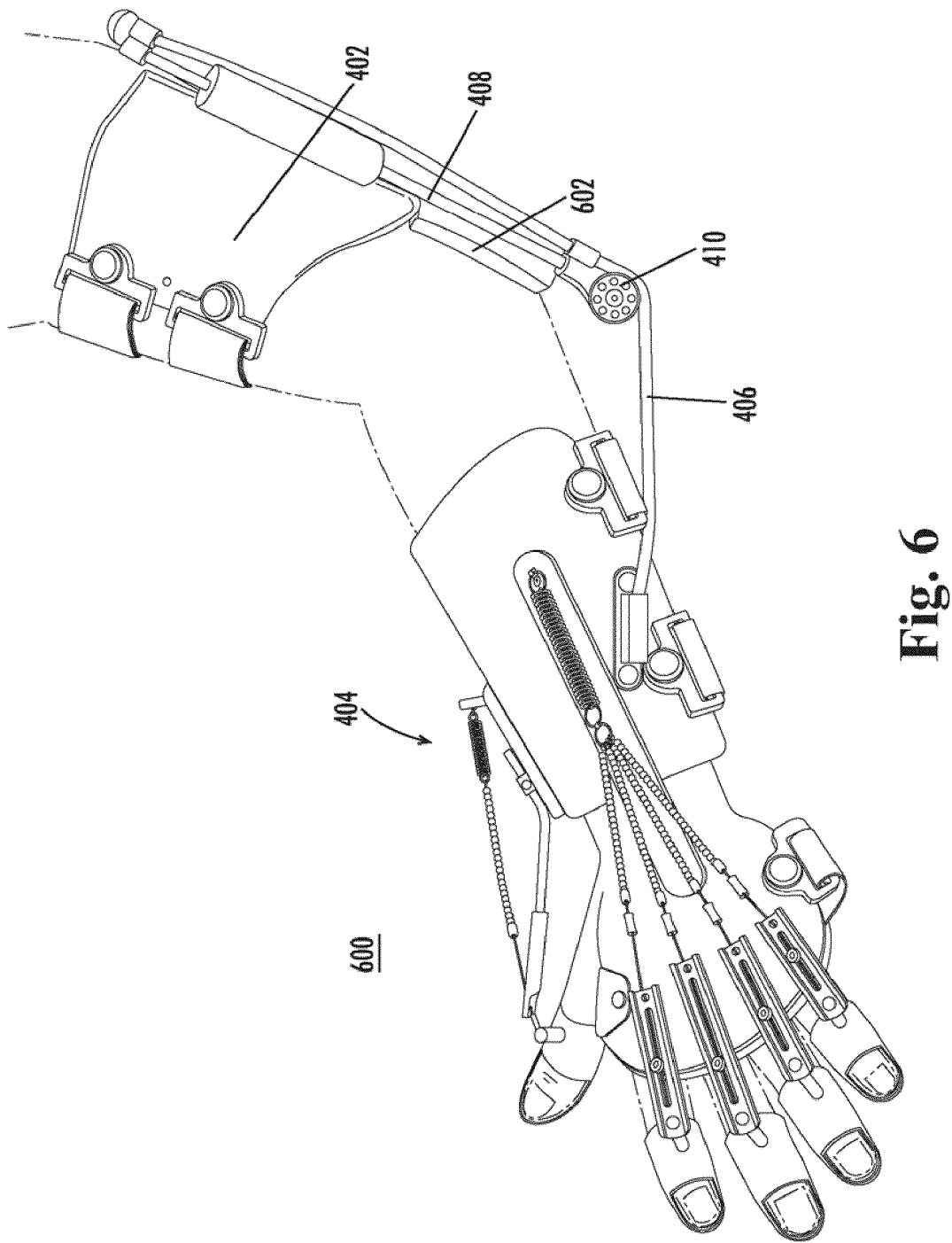
FIG. 6 is a perspective view of an elbow orthotic in accordance with another preferred embodiment of the present invention.

Referring now to the drawings and, in particular, FIGS. 4-6, one or more preferred embodiments of the present invention are next described. The following description of one or more preferred embodiments is merely exemplary in nature and is in no way intended to limit the invention, its implementations, or uses.

In this regard, FIG. 4 is a perspective view of an elbow orthotic 400 in accordance with a preferred embodiment of the present invention, wherein the arm is in an extended position; and FIG. 5 is a perspective view of the elbow orthotic 400 wherein the arm is in a flexed position. Additionally, FIG. 6 is a perspective view of an elbow orthotic 600 in accordance with another preferred embodiment of the present invention that is similar in construction and design to orthotic 400, but that further includes a padding component 602 as part of the orthotic 600.

In general, an orthotic of the present invention preferably comprises: an upper arm component that is configured to be secured to the upper arm above the elbow; and a lower arm component that is configured to be secured to the lower arm below the elbow. In particular, the lower arm section is secured to the wrist; to the wrist and hand; or to the wrist, hand, and fingers, as shown in FIG. 4.

Figure 7:
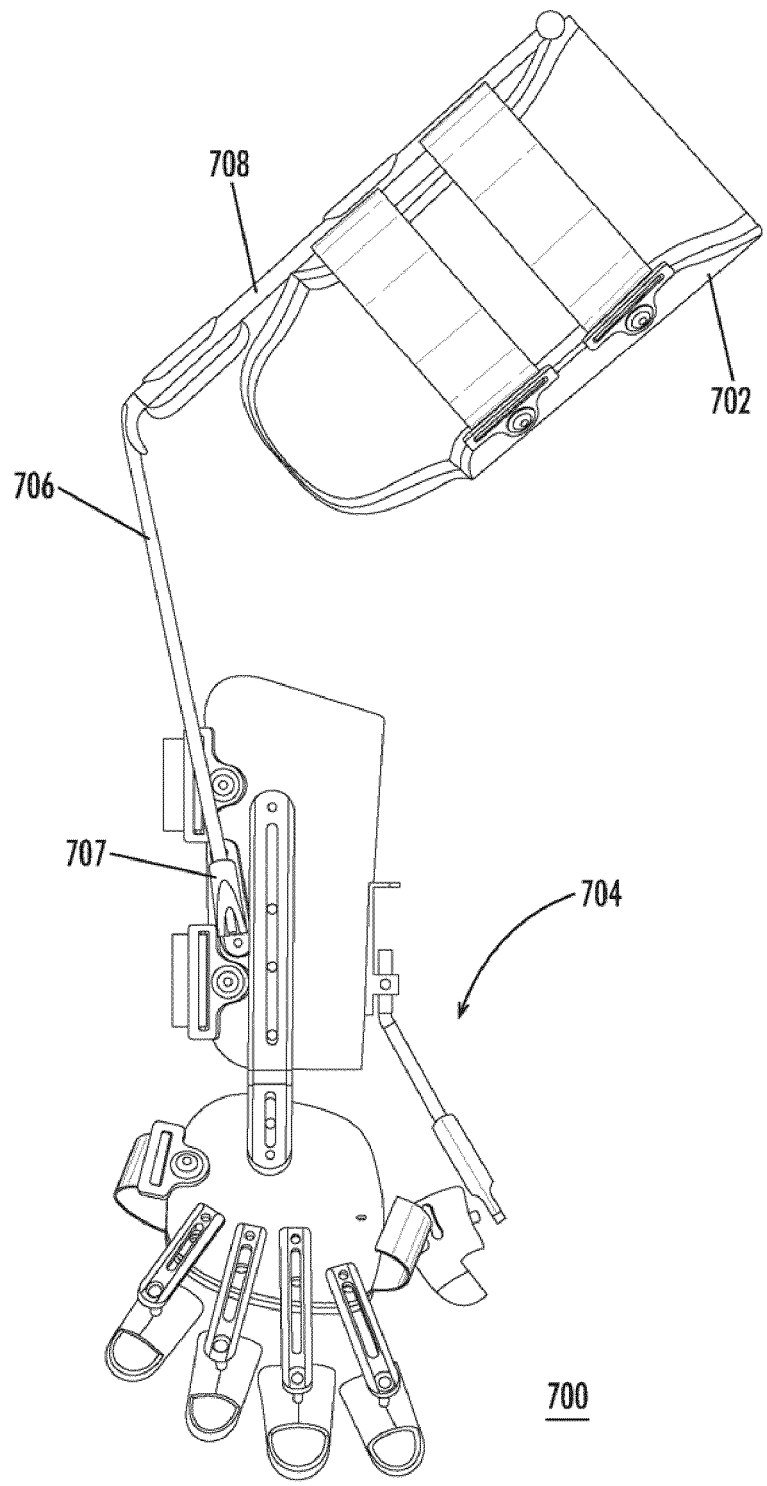
FIGS. 7-11 are different perspective views of an orthotic in accordance with another preferred embodiment of the invention.
Figure 8:
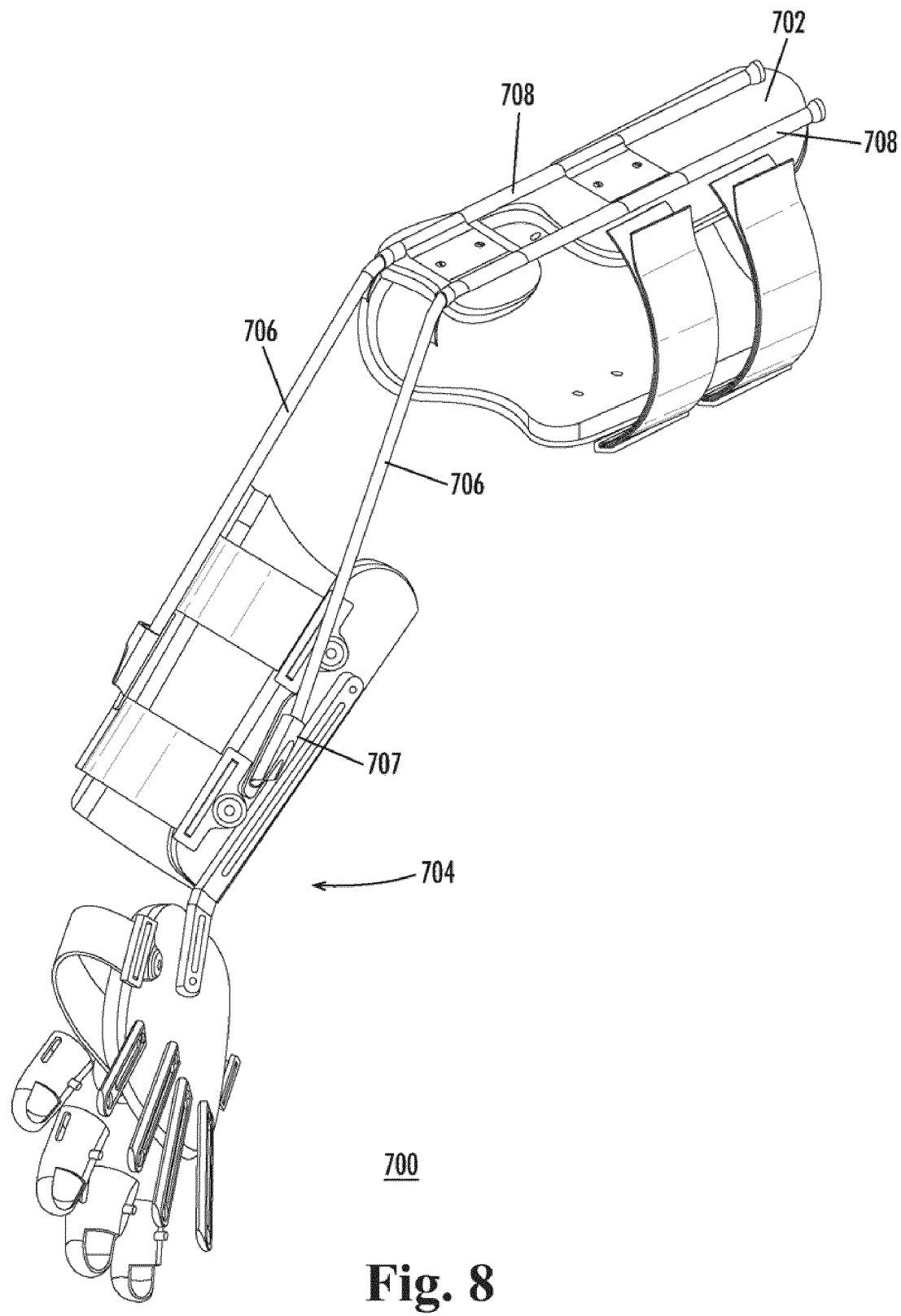
Figure 9:
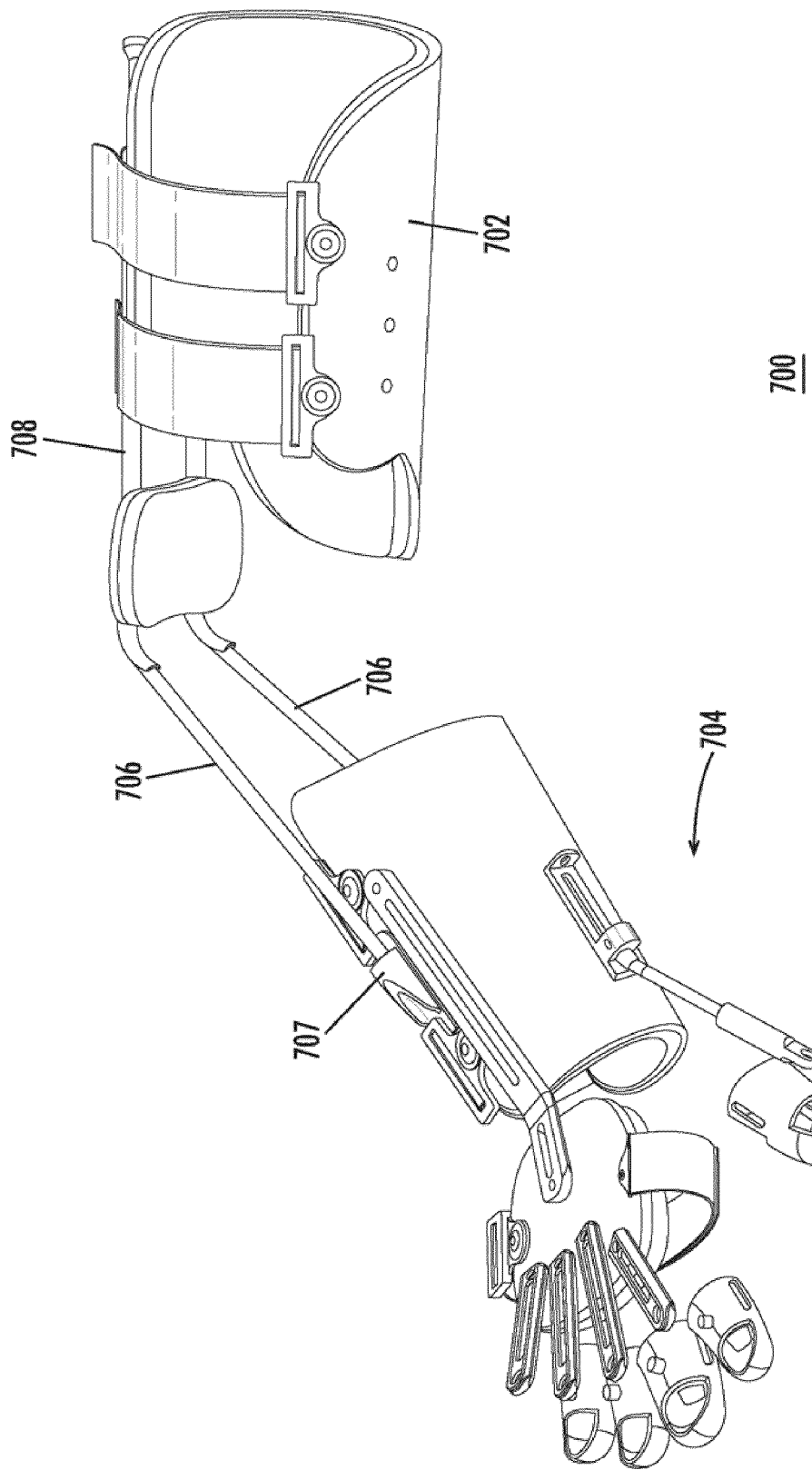
Figure 10:
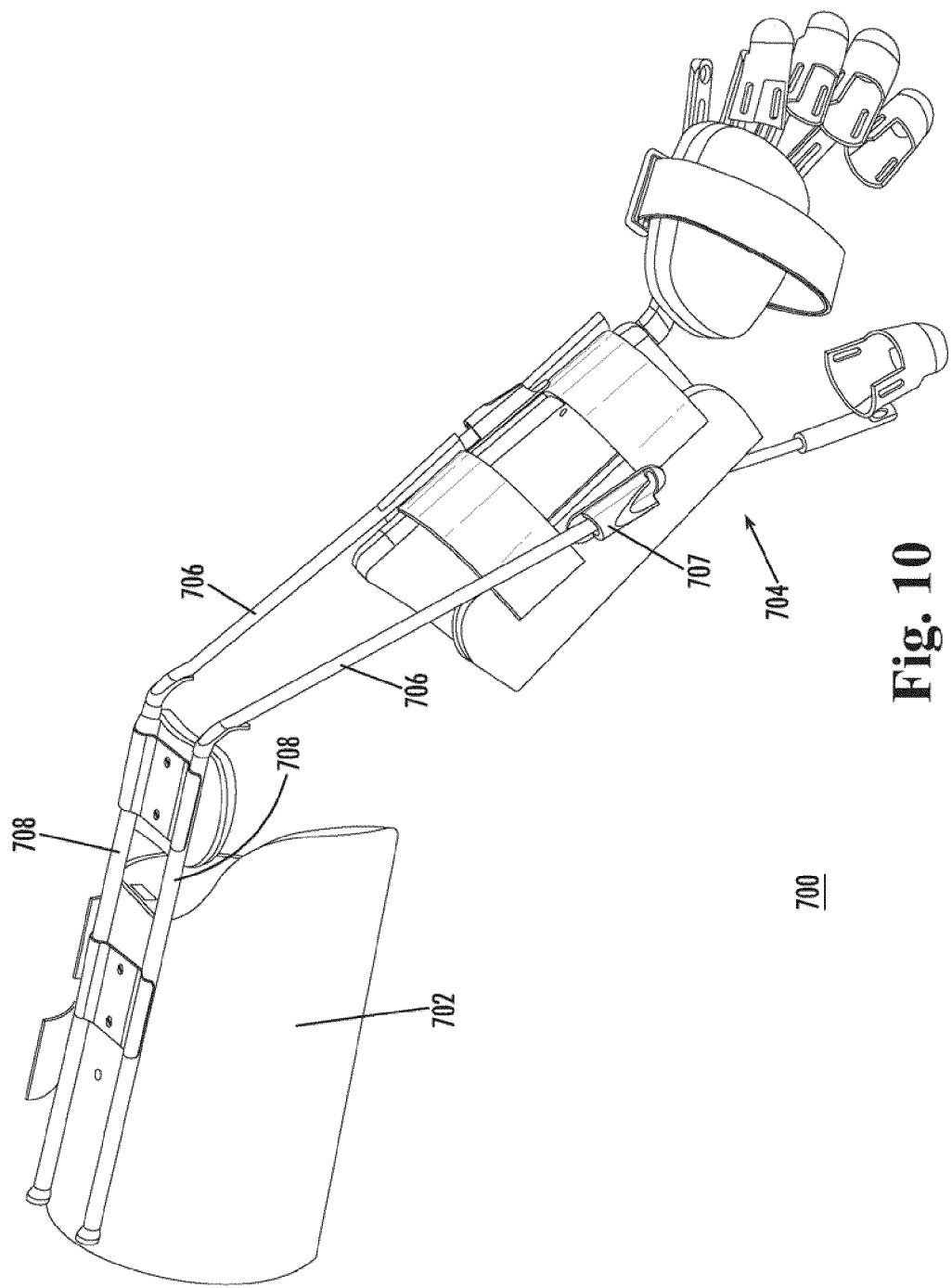
Figure 11:
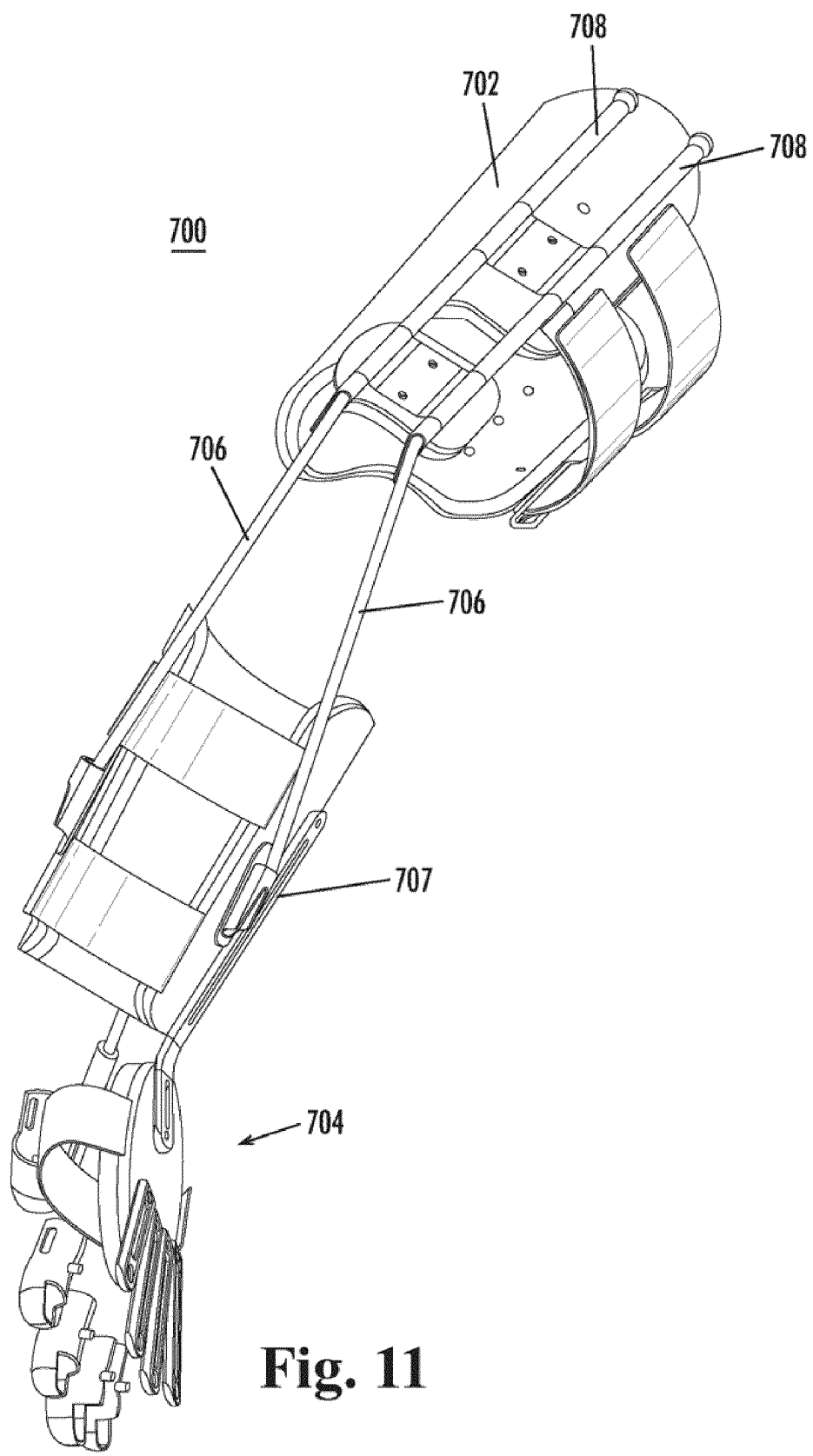

In the orthotics 400,600, the upper arm section preferably is in the form of a cuff 402 that is approximately 4 to 6 inches in length. As shown in FIGS. 4 and 7, upper cuff 402 may have either a anterior or lateral opening in order to secure the cuff to the user's upper arm. The cuff is secured to the arm with one or more attachments such as straps, clasps, buckles, or the like. The lower arm component itself comprises forearm-wrist-hand orthotics 404 substantially as shown and described in U.S. Pat. No. 7,001,352, which is hereby incorporated herein by reference; however, other designs of the lower arm component are certainly with the scope of the present invention, and the invention is not limited to use only of orthotics 404 of this patent.

In accordance with the present invention, upper arm component 402 and lower arm component 404 are connected by one or more elongate members 406. In contrast to conventional elbow orthotics, the upper and lower arm components are not hinged together.

In the illustrated embodiments of FIGS. 4-6, the elongate members comprise elastic cords 406 each of which provides a line of tension in the orthotic that tends to bias the upper and lower arm components toward a particular orientation relative to one another. In particular, elastic cord 406 is attached both to upper arm component 402 and to lower arm component 404. The attachments of elastic cord 406 can be accomplished, for example, using hooks, cleats, cams, clips, and the like. In the embodiment shown in FIG. 4, cleats 407 and 409 are used.

Furthermore, an outrigger 408 is attached to the posterior and/or lateral aspects of cuff 402 and can be adjustably mounted in the proximal and/or distal directions via additional attachment openings in the cuff. Outrigger 408 serves to guide each elastic cord 406 from cuff 402 to a point located below the apex of the elbow, from which elastic cord 406 extends and is attached to lower arm component 404. This arrangement assists with pulling the elbow into an extension position. Outrigger 408 thus defines a point of tensional redirection that is located below the elbow. In a variation not shown, but which will be apparent to the ordinary artisan over the drawings disclosed and described herein, another attachment to the cuff may be provided that locates the point of tensional redirection above the apex of the elbow in order to assist the elbow into a flexed position. The tensional redirection of an elastic cord is achieved in the preferred embodiment by means of a pulley 410, i.e., a freely rotatable wheel mounted at the distal end of the outrigger. FIGS. 7-16 shows another embodiment where redirection is achieved by a fixed end of outrigger 408.

When using elastic/shock cords to facilitate elbow extension, it is preferred that the cord or cords attach to outrigger 408 on upper component 402, with a cord (or more cords if using more than one cord) passing down outrigger 408, passing behind and being redirected below the apex of the elbow, and extending and attaching to lower component 404. The adjustable force generated in various flexed positions will help pull the elbow back into an extension position. In this case, the tension/force mimics the non-functioning muscle (triceps) that moves the elbow into extension. It also provides resistance to the weakened non-functioning muscle (biceps) that moves the elbow into flexion, thus assisting with strengthening.

When using elastic/shock cords to facilitate elbow flexion, it is preferred that the cord or cords attach to a site on the posterior or lateral aspect of upper arm component 402, with a cord (or more cords if using more than one cord) passing above and being redirected above the apex of the elbow, and extending to attach to lower arm component 404. The adjustable force then generated will help pull the elbow into a flexed position. In this case, the tension/force mimics the non-functioning muscle (biceps) that moves the elbow into flexion. It also provides resistance to the weakened non-functioning muscle (triceps) that moves the elbow into extension, thus assisting with strengthening.

The attachment sites on the lower component may also allow for force/tension adjustments, such as when cleats/cams 407 are used in conjunction with elastic/shock cords (e.g. when pulling the elastic cord further through the cleat thus increasing the tension/force).

As an alternative to elastic-cord 406 and -pulley 410, an elongate energy storing material like spring steel or a flex rod may be used as the elongate member for connecting and biasing the upper and lower arm sections toward a particular orientation relative to one another. Various energy storing materials may be used, and different forces will be generated depending on the respective physical properties of such materials (e.g. a ⅛ of an inch diameter elastic/shock cord will offer less force than a 3/16 of an inch diameter elastic/shock cord).

Outrigger 408 may also incorporate a padding component 602 at the posterior aspect of the elbow, as shown in FIG. 6. Padding component 602 helps maintain the position of upper cuff 402 and lower cuff 404 is moved.

Figure 12:
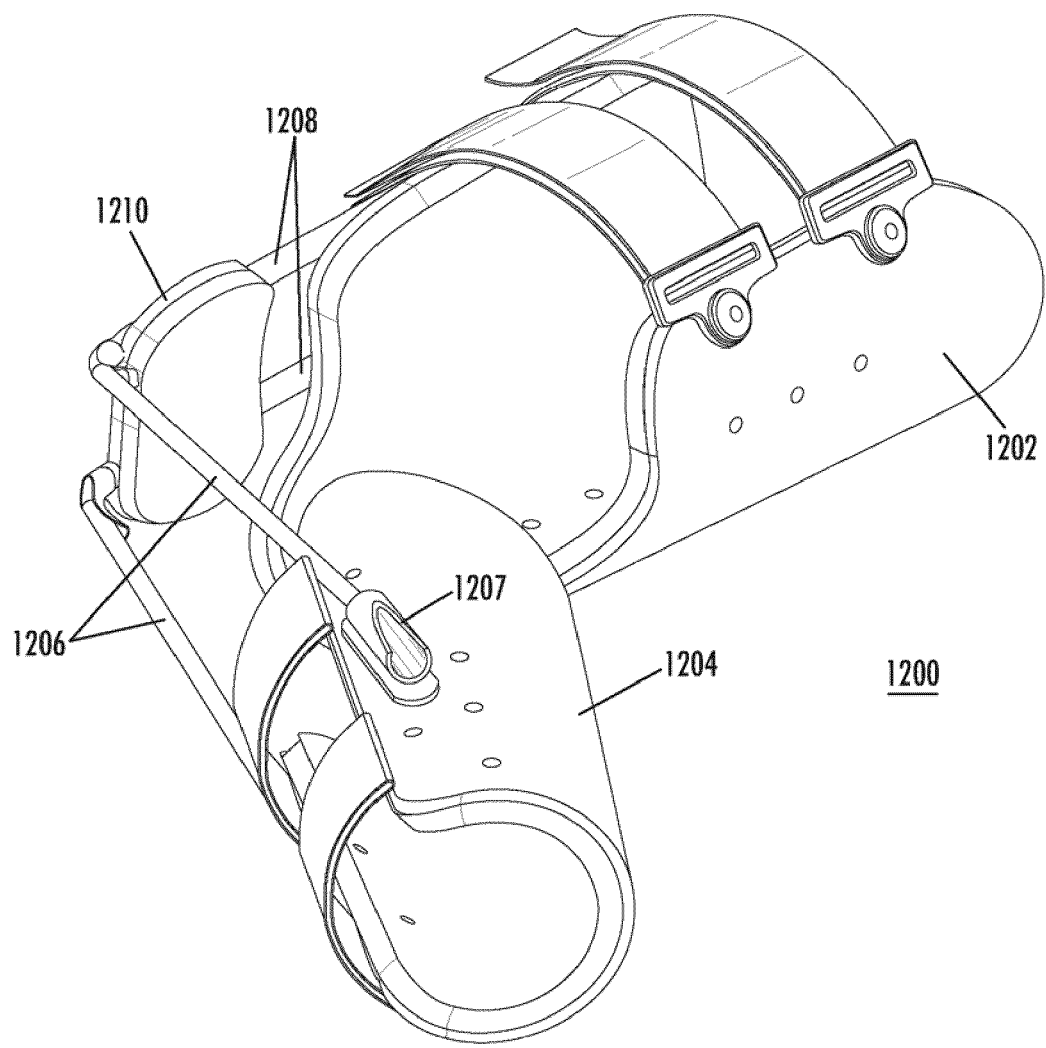
FIGS. 12-13 are different perspective views of another orthotic in accordance with a preferred embodiment of the invention.
Figure 13:
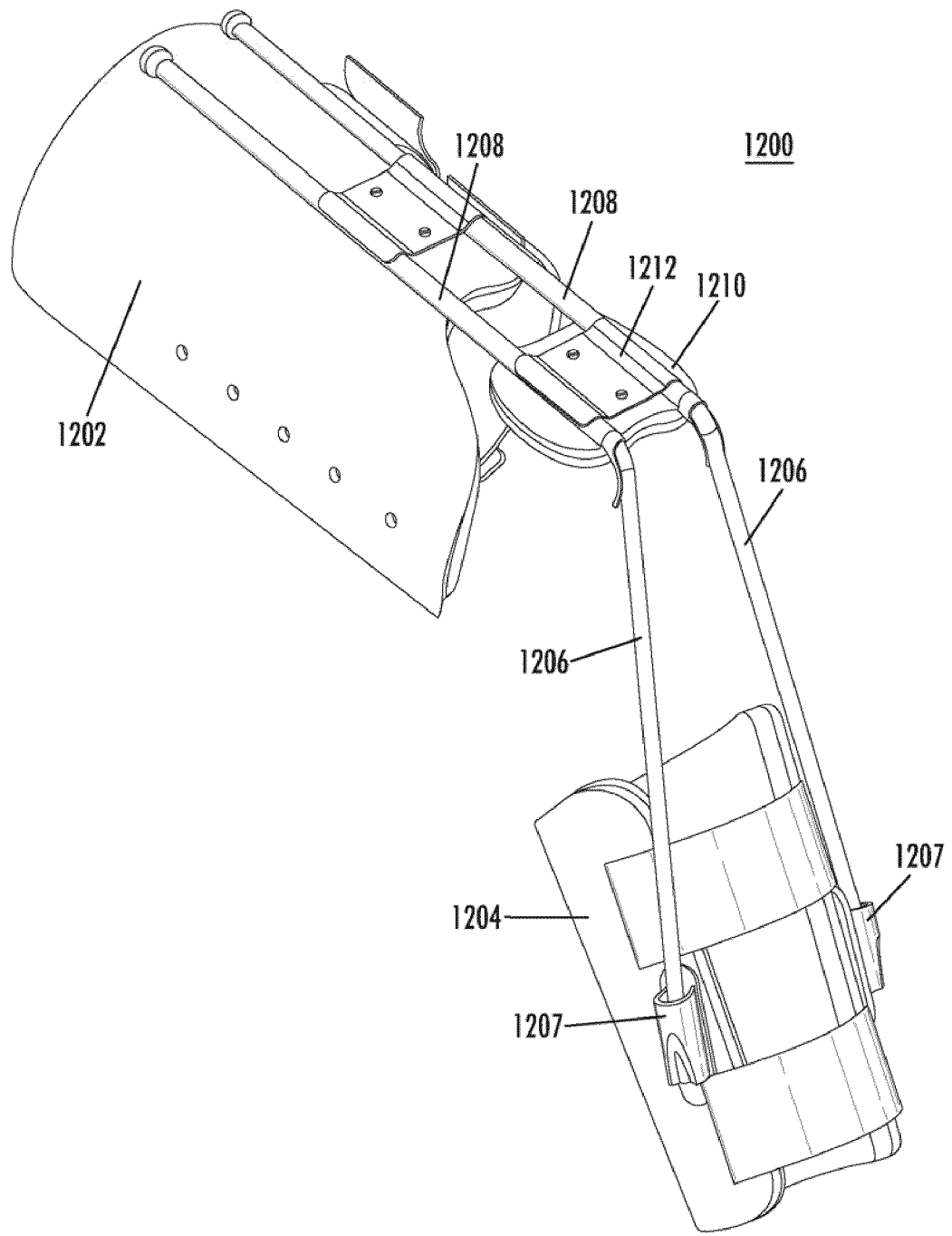

Still yet, FIG. 7-11 are different perspective views of an orthotic 700 in accordance with another preferred embodiment of the invention. This orthotic 700 is similar to orthotic 400 in that it has an upper cuff 702, lower arm component 704 that attaches to the forearm and hand and further spans the wrist. An outrigger 708 is releasably coupled to upper cuff 702 similar to that in the embodiments shown in FIGS. 4-6. Elastic cord 706 coupled upper cuff 702 to lower cuff 704. In contrast, FIGS. 12-13 are different perspective views of another orthotic 1200 in accordance with a preferred embodiment of the invention, wherein lower arm component 704 attaches only to the forearm. In this embodiment, upper cuff 1202 has two outriggers 1208 that redirect elastic cords 1206.

Cords 1206 connect to lower cuff 1204 by cleats 1207 (only one is shown in the figure). A pad 1210 is coupled to outrigger 1208 to provide additional upper arm support. As shown in FIG. 13, pad 1210 is secured to outrigger 1208 by an adjustable spring clamp 1212.

Figure 14:
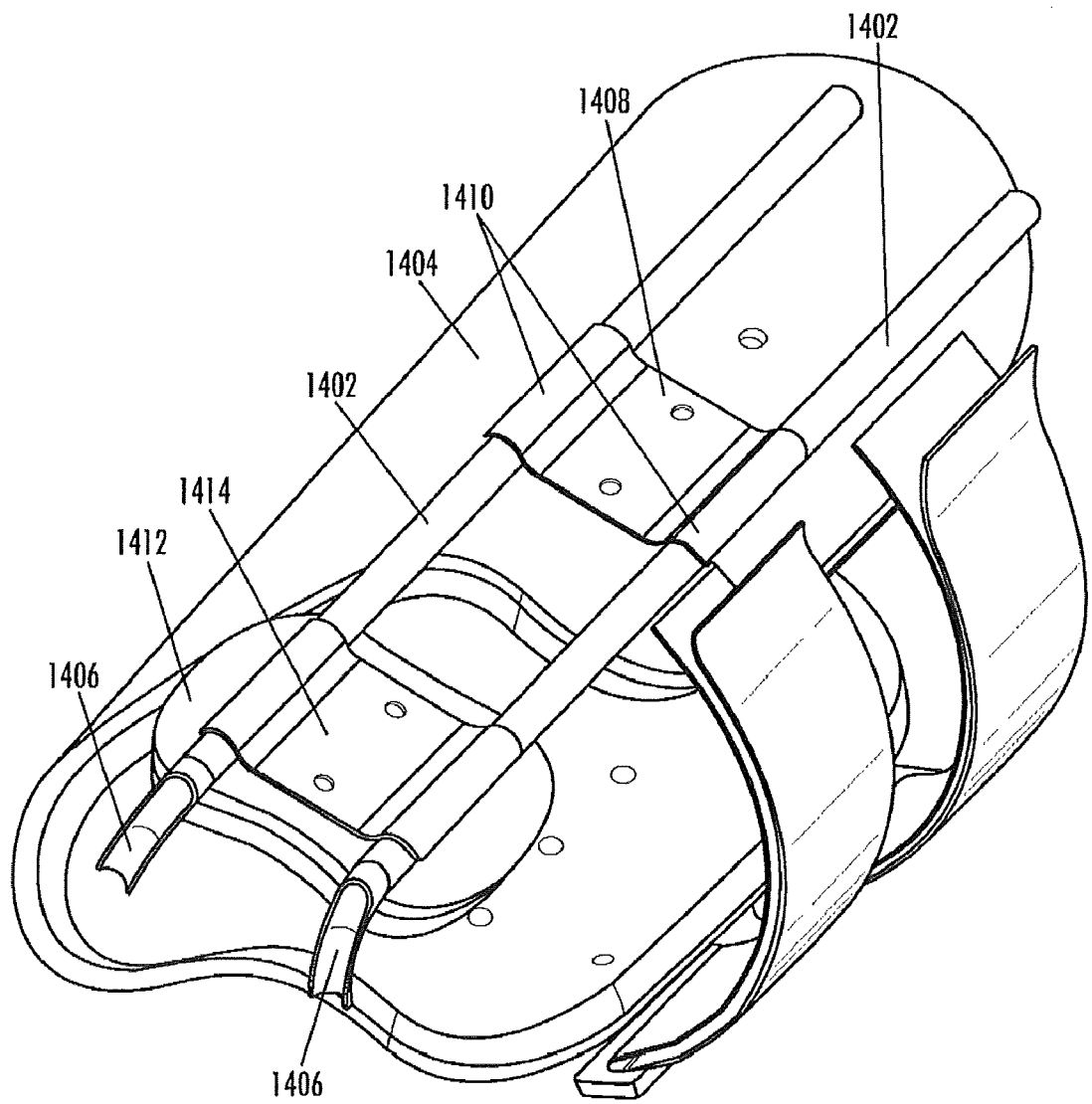
FIG. 14 illustrates an upper arm component in accordance with a preferred embodiment of the invention.
Figure 15:
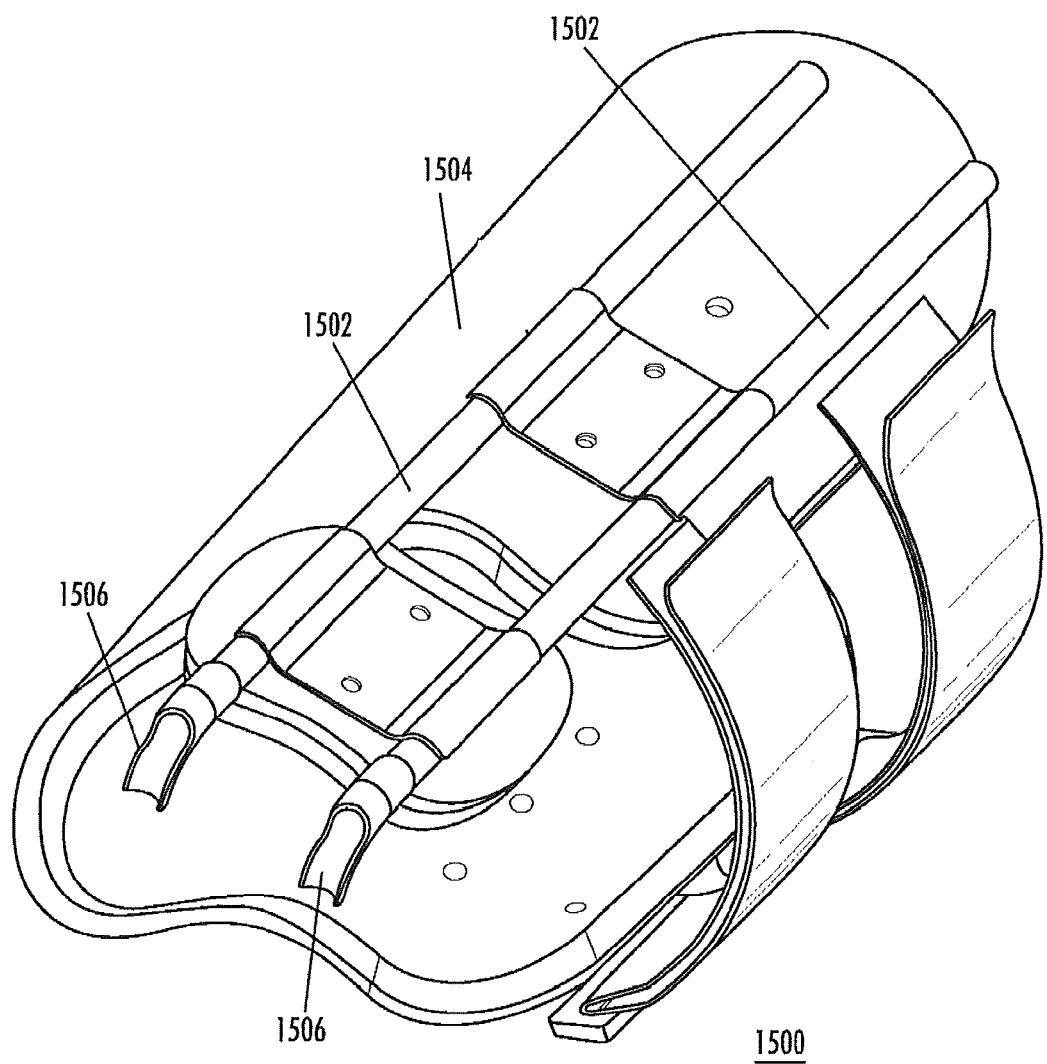
FIG. 15 illustrates an upper arm component in accordance with another preferred embodiment of the invention.
Figure 16:
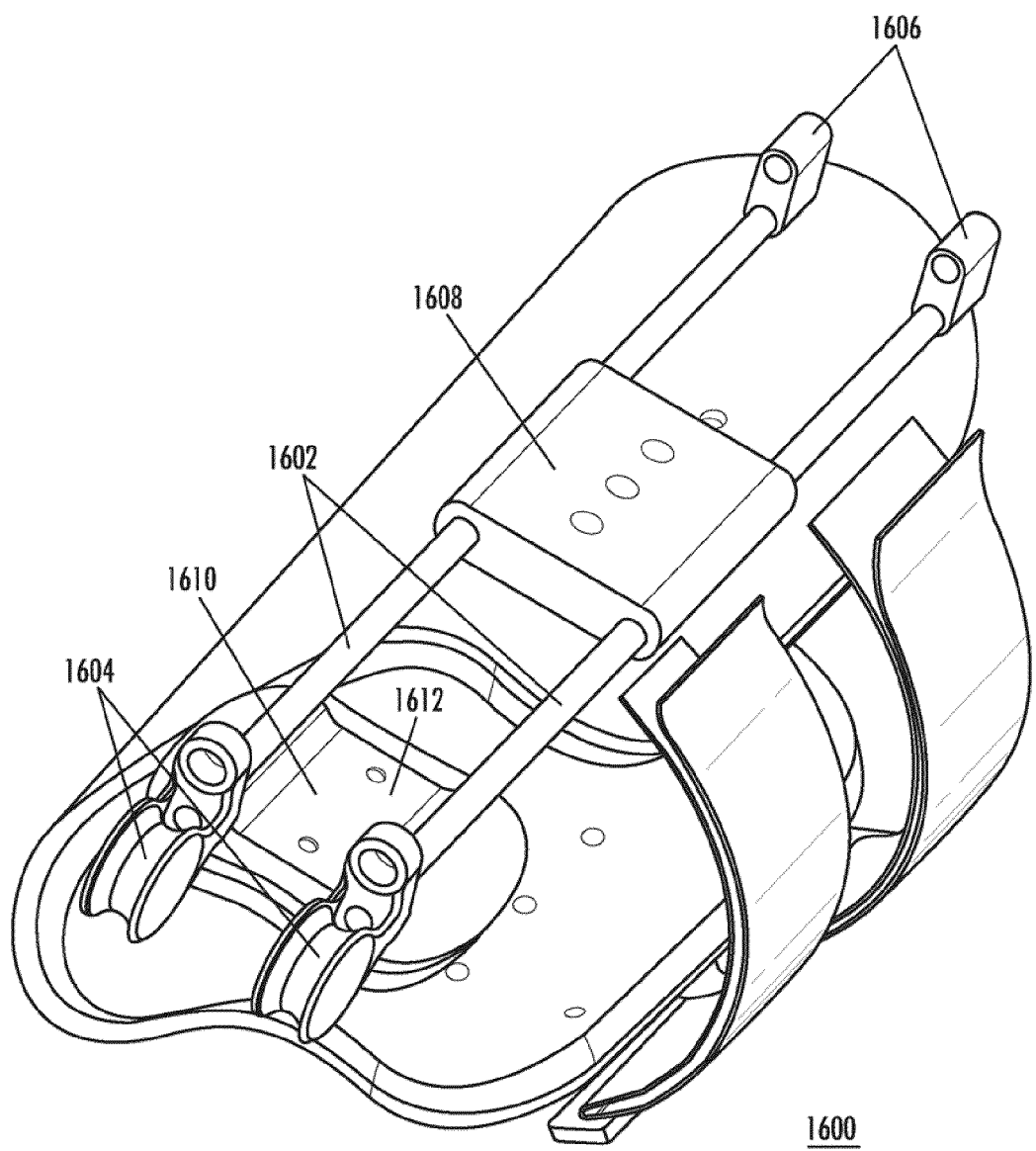
FIG. 16 illustrates an upper arm component in accordance with still another preferred embodiment of the invention.

FIGS. 14-16 illustrate variations of the upper arm component. In FIG. 14, upper arm component 1400 has conduit guides 1402 that are attached to cuff 1404 by adjustable spring plates 1408 and 1414 and that receive therethrough the elastic cords (not shown for clarity). Moreover, the elastic cords are guided by bent or curved sections outrigger end sections 1406 located proximate to the end of the conduit guides as shown in FIG. 14. For reference, upper arm component 1400 of FIG. 14 is utilized in the orthotic 700 of FIGS. 7-11.

In contrast, FIG. 15 is intended to illustrate an upper arm component 1500 having telescoping conduit guides, in that the bent or curved sections 1506 located at the end of the conduit guides 1502 actually extend within the conduit guides 1502 in frictional fit therewith and may pulled out to lengthen the protraction of the curved sections 1506 from cuff 1504, whereby the point of tensional redirection can be adjusted and positioned as desired along the direction of the axes of the conduit guides.

In the structural design of the upper arm component 1400, 1500 of FIGS. 14 and 15, the conduit guides are removably attached to the cuff by spring plate 1408, which includes curved sides 1410 that receive and retain the conduit guides against the cuff but that may be raised so as to release and remove the conduit guides from the cuff. Furthermore, as shown, a padding component 1412 is adjustably attached to the conduit guides via a second spring plate 1414.

FIG. 16 illustrates another upper arm component 1600 in accordance with another preferred embodiment thereof. In this embodiment, outriggers 1602 are provided with pulleys 1604 attached at their distal ends. Proximal ends of the outriggers (i.e., the opposite ends thereof) include retention members 1606 for receiving and retaining ends of the elastic cords (not shown for clarity) that are used to connect the upper and lower components together in an orthotic, which elastic cords are engaged and redirected by the pulleys. Outriggers 1602 is secured to the cuff by a mounting member 1608 and the outrigger preferably is adjustable along the axis thereof by sliding frictional engagement through bores formed in mounting member 1608. A padding component 1610 also is releasably mounted to outriggers 1602 using a spring plate 1612 and, in FIG. 16, spring plate 1612 and padding component 1610 are actually shown in a disengaged state with padding component 1610 disposed below outriggers 1602. Padding component 1610 is secured to spring plate 1612 using conventional fasteners, such as screws.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed:

1. An orthotic for mounting on a user's arm:
   a. an upper cuff removeably attachable the user's arm at a point above an elbow joint and adapted to be substantially rotationally fixed to the upper arm, wherein said upper cuff defines a first longitudinal axis extending through said upper cuff;
   b. a lower cuff removeably attachable to the user's arm at a point below the elbow joint and adapted to be substantially rotationally fixed to said forearm, wherein said lower cuff defines a second longitudinal axis extending through said lower cuff;
   c. at least one flexible elongated member having a first end and an opposite second end,
      i. said elongated member first end being releasably coupled to said upper cuff, and
      ii. said elongated member second end being releasably coupled to said lower cuff; and
   d. an outrigger moveably coupled to said upper cuff and configured to redirect said at least one flexible elongated member.

2. The orthotic of claim 1, wherein said lower cuff rotates substantially about said second axis with respect to said upper cuff.

3. The orthotic of claim 1, further comprising a plate releasably coupled to said upper cuff that when in one position axially and rotationally maintains said outrigger to said upper cuff and when in a second position allows said outrigger to axially and rotationally move with respect to said upper cuff.

4. The orthotic of claim 3, wherein said outrigger first end defines a cleat for receiving and maintaining the connection of said at least one flexible elongated member to said upper cuff.

5. The orthotic of claim 1, wherein said outrigger has a first end that is mounted proximate to said upper cuff and a second end that is proximate said lower cuff, said second end defining an annular pulley.

6. The orthotic of claim 5, wherein said annular pulley is rotationally fixed with respect to said outrigger.

7. The orthotic of claim 1, wherein said at least one flexible elongated member is chosen from an elastomer cord, a flexible rod and a polymer cord.

8. The orthotic of claim 1, wherein said at least one flexible elongated member is mounted to said upper and lower cuffs so as to urge the user's arm into one of extension and flexion.

9. The orthotic of claim 1, further comprising a pad support mounted intermediate said upper cuff and said lower cuff so that said pad support contacts the user's arm above the elbow.

10. The orthotic of claim 9, wherein said pad support is releasably mounted on said outrigger so that the location of said pad support may be changed according to the user's physical characteristics.

11. An orthotic for mounting on a user's arm about the user's elbow joint comprising:
    a. an upper cuff removeably attachable to the user's arm at a point above the elbow joint, adapted to be substantially rotationally fixed to the upper arm;
    b. a lower cuff removeably attachable to the user's arm at a point below the elbow joint, adapted to be substantially rotationally fixed to the user's forearm, wherein said lower cuff defines a second longitudinal axis extending through said lower cuff;
    c. an outrigger having a first end releasably attached to said upper cuff by a releasable clamp so that said outrigger may be adjusted with respect to said upper cuff when said releasable clamp is in a first position and is axially fixed to said upper cuff when said releasable clamp is in a second position and a second end; and
    d. at least one flexible elongated member having a first end and an opposite second end,
       i. said at least one flexible elongated member first end being releasably coupled to said outrigger first end, and
       ii. said at least one flexible elongated member second end being releasably and adjustably coupled to said lower cuff so that the amount of tension provided by said at least one flexible elongated member,
    wherein said upper cuff and said lower cuff moves in more than one plane with respect to one another.

12. The orthotic of claim 11, wherein said outrigger second end is configured to redirect tension exerted by said at least one flexible elongated member depending on the position of said outrigger with respect to said upper cuff to cause one of flexion and extension of the user's arm.

13. The orthotic of claim 11, wherein said at least one flexible elongated member is chosen from an elastomer cord, a flexible rod and a polymer cord.

14. An orthotic for mounting on a user's arm comprising:
    a. an upper cuff removeably attachable to the user's arm at a point above the elbow joint;
    b. a lower cuff removeably attachable to the user's arm at a point below the elbow joint and substantially rotationally fixed to said forearm;
    c. at least one flexible elongated member having a first end and an opposite second end,
       i. said elongated member first end being releasably coupled to said upper cuff, and
       ii. said elongated member second end being releasably coupled to said lower cuff; and
    d. an outrigger moveably coupled to said upper cuff and configured to redirect a tensional force exerted by said at least one flexible elongated member,
    wherein said upper cuff and said lower cuff moves in more than one plane with respect to one another.

15. The orthotic of claim 14, further comprising a pad support moveably mounted on said outrigger so that the position of said pad support may be changed according to the user's physical characteristics.

* * * * *